(12) United States Patent
Dubois

(10) Patent No.: US 9,187,387 B2
(45) Date of Patent: Nov. 17, 2015

(54) METHOD FOR PREPARING FLUORINATED OLEFIN COMPOUNDS

(71) Applicant: Jean-Luc Dubois, Millery (FR)

(72) Inventor: Jean-Luc Dubois, Millery (FR)

(73) Assignee: Arkema France, Colombes (FR)

( * ) Notice: Subject to any disclaimer, the term of this patent is extended or adjusted under 35 U.S.C. 154(b) by 0 days.

(21) Appl. No.: 14/366,853

(22) PCT Filed: Nov. 29, 2012

(86) PCT No.: PCT/FR2012/052752
§ 371 (c)(1),
(2) Date: Jun. 19, 2014

(87) PCT Pub. No.: WO2013/093272
PCT Pub. Date: Jun. 27, 2013

(65) Prior Publication Data
US 2014/0364658 A1 Dec. 11, 2014

(30) Foreign Application Priority Data
Dec. 22, 2011 (FR) ..................... 11 62314

(51) Int. Cl.
*C07C 17/25* (2006.01)
*C07C 17/087* (2006.01)
*C07C 17/158* (2006.01)
*C07C 17/20* (2006.01)

(52) U.S. Cl.
CPC ............... *C07C 17/25* (2013.01); *C07C 17/087* (2013.01); *C07C 17/158* (2013.01); *C07C 17/206* (2013.01); *C07C 2523/26* (2013.01)

(58) Field of Classification Search
CPC .... C07C 17/25; C07C 17/206; C07C 17/087; C07C 17/158; C07C 2523/26
USPC ................................................... 570/156, 160
See application file for complete search history.

(56) References Cited

U.S. PATENT DOCUMENTS

| 8,207,383 B2 * | 6/2012 | Deur-Bert et al. ............ 570/169 |
| 8,563,789 B2 * | 10/2013 | Elsheikh et al. ............. 570/160 |
| 8,614,361 B2 * | 12/2013 | Suzuki et al. ................. 570/156 |
| 8,816,140 B2 * | 8/2014 | Karube et al. ................ 570/156 |
| 2011/0245548 A1 | 10/2011 | Merkel et al. |
| 2013/0035526 A1 * | 2/2013 | Elsheikh et al. ............. 570/156 |

FOREIGN PATENT DOCUMENTS

| CN | 102001911 A | 4/2011 |
| WO | 2007/079431 A2 | 7/2007 |
| WO | 2008/040969 A2 | 4/2008 |
| WO | 2008/054781 A1 | 5/2008 |
| WO | 2008/075017 A2 | 6/2008 |
| WO | 2009/084703 A1 | 7/2009 |
| WO | 2010/123154 A2 | 10/2010 |
| WO | WO 2011/130108 | 10/2011 |

OTHER PUBLICATIONS

International Search Report for PCT/FR2012/052752, dated Mar. 5, 2013.

* cited by examiner

*Primary Examiner* — Shailendra Kumar
(74) *Attorney, Agent, or Firm* — Brinks Gilson & Lione

(57) ABSTRACT

The present invention relates to a method for preparing fluorinated olefin compounds, in particular (chloro)fluoropropenes and (chloro)fluorobutenes, and specifically, the fluorinated compound 2,3,3,3-tetrafluoro-1-propene, including at least one step of fluorination, in the gaseous phase, with HF and at least one compound selected from the halopropenes having formula the $CX_3CHClCH_2X$ and the halopropenes having the formulas $CX_3CC_1=CH_2$, $CClX_2CCl=CH_2$ and $CX_2=CClCH_2X$, where X is, independently, a fluorine or chlorine atom, in the presence of oxygen and a fluorination catalyst suspended in a fluidized-bed reactor.

10 Claims, No Drawings

METHOD FOR PREPARING FLUORINATED OLEFIN COMPOUNDS

FIELD OF THE INVENTION

A subject matter of the invention is a process for the preparation of fluoroolefin compounds, in particular (chloro)fluoropropenes and (chloro)fluorobutenes and more particularly the fluorinated compound 2,3,3,3-tetrafluoro-1-propene (HFO-1234yf).

TECHNOLOGICAL BACKGROUND

Hydrofluorocarbons (HFC) and in particular hydro-fluoroolefins, such as 2,3,3,3-tetrafluoro-1-propene (HFO-1234yf) are compounds known for their properties of refrigerants and heat-exchange fluids, extinguishers, propellants, foaming agents, blowing agents, gaseous dielectrics, monomer or polymerization medium, support fluids, agents for abrasives, drying agents and fluids for energy production units. Unlike CFCs and HCFCs, which are potentially dangerous to the ozone layer, HFOs do not comprise chlorine and thus do not present a problem for the ozone layer.

Several processes for the manufacture of HFO-1234yf are known.

WO 2009/084703 describes a process for the manufacture of HFO-1234yf from hexafluoropropene involving the intermediacy of hexafluoropropane, pentafluoropropene, and pentafluoropropane.

WO 2007/079431 describes the preparation of HFO-1234yf by a process comprising the stages of fluorination of 2-chloro-3,3,3-trifluoro-1-propene (HCFO-1233xf) to give 1,1,1,2-tetrafluoro-2-chloropropane (HFC-244bb), followed by a dehydrochlorination stage. The product HCFO-1233xf is prepared by fluorination of the corresponding chlorinated precursor ($CCl_2$=$CClCH_2Cl$).

WO 2008/054781 describes a preparation of HFO-1234yf by reaction of 2,3-dichloro-1,1,1-trifluoropropane (HFC-243db) in the presence of HF over a catalyst, in particular 98/2 Cr/Co. The reaction products comprise HFO-1234yf and 2-chloro-3,3,3-trifluoro-1-propene (HCFO-1233xf), the latter product being predominant; the other products 1-chloro-3,3,3-trifluoro-1-propene (HCFO-1233zd) and also 1,1,1,2,2-pentafluoropropane (HFC-245cb) and 1,3,3,3-tetrafluoro-1-propene (HFO-1234ze) are also formed. A higher temperature favors the production of the 1233zd isomer. The starting material, 2,3-dichloro-1,1,1-trifluoropropane (HFC-243db), is indicated as being obtained by chlorination of trifluoro-1-propene (TFP).

WO 2008/040969 and WO 2008/075017 describe a substantially similar preparation. It is indicated that the reaction proceeds by dehydrochlorination of HFC-243db to give HCFO-1233 (both xf and zd), followed by a reaction involving the formation of 1,1,1,2-tetrafluoro-2-chloropropane and the formation subsequently of the desired 2,3,3,3-tetrafluoro-1-propene by dehydrochlorination. The HF:organics ratio is varied and it is indicated that the dehydrochlorination reaction to give HCFO-1233 (xf and zd) is favored by low HF:organics ratios while the reaction for the preparation of the desired final compound is favored by high HF:organics ratios. The starting material, 2,3-di-chloro-1,1,1-trifluoropropane (HFC-243db), is indicated as being obtained by chlorination of trifluoropropene or trifluoromethylpropene.

WO 2010/123154 describes a preparation of HFO-1234yf by reaction of HCFO-1233xf with HF in the presence of oxygen and of a catalyst comprising chromium oxide $CrO_m$ with $1.5<m<3$. This document teaches the use of an oxygen/HCFO-1233xf molar ratio at most equal to 1 in order to improve the selectivity.

Furthermore, the document US 2011/245548 describes the use of a molar ratio of oxygen with respect to a chlorinated compound of between 0.1 and 1 in order to increase the lifetime of a catalyst in the fluorination reaction of pentachloropropane or tetrachloropropene to give HCFO-1233xf.

The preparation methods as mentioned above generally comprise several stages and require very expensive capital costs. In addition, it is often complex to implement them on an industrial scale. The presence of byproducts which cannot be recovered in value and also the lifetime of the catalyst are among the most frequently encountered problems when moving on to the industrial scale.

Furthermore, the presence of oxygen in an amount as described in the prior art presents numerous problems: formation of oxygen-comprising byproducts; formation of water, which, in the presence of HF, results in a highly corrosive medium and safety (risk of ignitibility of the gaseous effluent) in the reactor or downstream of the reactor in the separation units.

There exists a need for a process for the preparation of HFO-1234yf from a starting material which is readily accessible and easy to employ, resulting "on a long-term basis" in the desired product with a high selectivity and advantageously a high yield and/or conversion.

SUMMARY OF THE INVENTION

The invention thus provides a process for the preparation of 2,3,3,3-tetrafluoro-1-propene by gas-phase fluorination with HF of at least one compound chosen from halopropanes of formula $CX_3CHClCH_2X$, and halopropenes of formulae $CX_3CCl$=$CH_2$, $CClX_2CCl$=$CH_2$ and $CX_2$=$CClCH_2X$, with X independently representing a fluorine or chlorine atom, in the presence of molecular oxygen and of a fluorination catalyst held in suspension in a fluidized bed reactor.

According to one embodiment, the halopropane is chosen from 2,3-dichloro-1,1,1-trifluoropropane and/or 1,1,1,2,3-pentachloropropane (HFC-240db).

According to one embodiment, the halopropene of formula $CX_3CCl$=$CH_2$ is chosen from 2-chloro-3,3,3-trifluoro-1-propene.

According to one embodiment, the HF/compounds to be fluorinated ratio is superstoichiometric.

According to one embodiment, the reaction inter-mediates of 2,3,3,3-tetrafluoro-1-propene are recycled to the reactor.

DETAILED DESCRIPTION OF THE EMBODIMENTS

The invention uses a stage of gas-phase fluorination with HF and of at least one compound chosen from halopropanes of formula $CX_3CHClCH_2X$, and halopropenes of formulae $CX_3CCl$=$CH_2$, $CClX_2CCl$=$CH_2$ and $CX_2$=$CClCH_2X$, with X independently representing a fluorine or chlorine atom, in the presence of molecular oxygen and of a fluorination catalyst held in suspension in a fluidized bed reactor.

The molecular oxygen can be in the form of air, enriched air or high-purity oxygen.

According to the invention, this stage is carried out in particular under a pressure of greater than 1.5 bar absolute. Advantageously, the pressure is between 2 and 15 bar, in particular between 2.2 and 5 bar.

The HF:compounds to be fluorinated molar ratio is between 50:1 and 1:1, preferably 30:1 and 5:1, advantageously between 25:1 and 5:1.

The reaction temperature can be highly variable. For example, it can be between 200 and 500° C., preferably between 250 and 400° C., advantageously between 275 and 380° C.

The oxygen:compounds to be fluorinated molar ratio is between 0.01 and 1, preferably between 0.05 and 0.2.

The contact time (ct) between the gas mixture comprising the reactants and the catalyst, defined in the present invention according to the formula below:

$$ct(s \cdot g/cm^3) = (W/F) \times (273/(273+T)) \times ((101325+P)/101325)$$

in which W represents the amount of catalyst in the fluidized bed in grams, F represents the velocity of the gas flow under standard temperature and pressure conditions, T represents the reaction temperature in ° C. and P represents the pressure in pascals, is preferably between 1 and 50 s and advantageously between 2 and 40 s.

The linear velocity of the gas flow comprising the reactants which is introduced into the fluidized bed reactor, defined in the present invention by the formula below:

$$Lv(cm/sec) = F \times ((273+T)/273) \times (101325/(101325+P)) \times S)$$

in which F, T and P are defined as above and S is the area of the internal cross section of the reactor (cm$^2$)—also known as empty column linear velocity—, is preferably between 0.5 and 200 cm/s and advantageously between 1 and 100 cm/s.

The gas flow of the reactants can be introduced into the reactor, partially or completely, by tangential injection, so as to create a controlled movement of turbulence through the fluid bed, in order thus to increase the contact time, to improve the homogeneity of the catalyst and/or to prevent the agglomeration of the catalyst particles.

The reaction product can be subjected to separation stages, such as distillation, washing, and the like, in a conventional manner known to a person skilled in the art.

According to the invention, the flow exiting from the fluidized reactor comprises HFO-1234yf and at least one compound chosen from 1,1,1,2,2-pentafluoropropane, 2-chloro-3,3,3-trifluoro-1-propene and 2-chloro-1,1,1,2-tetrafluoropropane.

This flow can additionally comprise HF and HCl.

The flow, after separation of HFO-1234yf and optionally HCl, is subsequently recycled to the reactor.

According to another aspect, the invention is a process for the preparation of HFO-1234yf from 1,1,1,2,3-pentachloropropane comprising a stage of gas-phase fluorination of 1,1,1,2,3-pentachloropropane with HF in the presence of molecular oxygen and of a fluorination catalyst held in suspension in a fluidized bed reactor, in order to give a flow comprising HFO-1234yf, 2-chloro-3,3,3-tri-fluoro-1-propene, 1,1,1,2,2-pentafluoropropane, HF and HCl, and a separation stage in which the HFO-1234yf and optionally HCl is separated from the flow before being recycled to the fluidized bed reactor.

The catalyst involved is, for example, a catalyst based on a metal, in particular on a transition metal or an oxide or halide or oxyhalide derived from such a metal. Catalysts are, for example, FeCl$_3$, chromium oxyfluoride, Ni (including Ni mesh), NiCl$_2$, CrF$_3$ and their mixtures, for example Ni—Cr/AlF$_3$. Other possible catalysts are catalysts supported on carbon, catalysts based on antimony, catalysts based on aluminum (such as AlF$_3$ and Al$_2$O$_3$ and aluminum oxyfluoride and fluorinated alumina), on palladium, on platinum, on rhodium and on ruthenium. Reference may be made to the list given in the document US-P-5396000, column 1, line 50, to column 2, line 2, or to the list given in WO2007/056194, page 16, lines 13-23. Use may also be made of the catalysts described in WO2008/040969 and in particular Zn on chromium oxide treated with HF.

Chromium-based catalysts are preferred.

The chromium-based catalysts can comprise at least one cocatalyst chosen from Co, Ti, V, Fe, Ge, As, Nb, Mo, Sb, W, Ta, P and Mn.

Mixed catalysts comprising chromium and at least one metal chosen from Ni, Mg and Zn are also preferred.

In order to improve the attrition of these catalysts, it is possible to incorporate compounds such as alumina or colloidal silica and/or to support the active material on or in fluidizable beads of silicon carbide.

The catalysts are advantageously employed in the powder form. They are generally obtained by atomization.

The mean diameter of the catalyst particles is preferably between 20 and 200 microns, advantageously between 2 and 80 microns.

The catalysts entrained by the flow of reactants, including the fine powders produced by attrition, are recovered by internal or external cyclones placed on the line for treatment of the effluents, and also by particle filters. After removing the fines, the catalysts recovered in the cyclone are subsequently returned to the reactor via an elutriation leg.

Advantageously, the catalysts are subjected to an activation treatment in the presence of a stream of oxidizing agent, such as air, oxygen or chlorine.

Advantageously, the catalysts are also subjected to an activation stage using a flow comprising hydrofluoric acid.

According to one embodiment, the activation of the catalysts can be carried out in two stages with a treatment with the oxidizing agent followed by that with HF.

According to another embodiment, the activation of the catalysts can be carried out in two stages with a treatment with HF followed by that with the oxidizing agent.

Depending on the catalyst or the reaction, it is possible to carry out this alternation several times (activations with a treatment with air followed by HF, again a treatment with air followed by HF, and so on).

The temperature of the treatment with the oxidizing agent can be between 250 and 500° C., preferably between 300 and 400° C., for a duration of between 10 and 200 hours.

The temperature of the treatment with HF can be between 100 and 450° C., preferably between 200 and 300° C., for a duration of between 1 and 50 hours.

According to another embodiment, the activation of the catalysts can be carried out in at least one stage with a treatment with the mixture of HF and oxidizing agent. The oxidizing agent can represent between 2 mol % and 98 mol %, with respect to the mixture of HF and oxidizing agent, and the activation temperature can vary between 200 and 450° C. for a duration of between 10 and 200 hours.

The catalyst activation can be continued by a fluorination reaction in the presence of an oxidizing agent, of HF and of at least one compound chosen from a halopropane(s) of formulae CX$_3$CHClCH$_2$X and CX$_3$CFXCH$_3$, and/or at least one halopropene(s) of formulae CX$_3$CCl=CH$_2$, CClX$_2$CCl=CH$_2$ and CX$_2$=CClCH$_2$X, with X independently representing a fluorine or chlorine atom. The HF/halopropane and/or halopropene molar ratio can be between 2 and 40. The oxidizing agent/halopropane and/or halopropene molar ratio can be between 0.04 and 2.5. The duration of this stage of activation by fluorination can be between 6 and 100 hours and the temperature can be between 300 and 400° C.

On conclusion of this activation stage, the catalyst is preferably subjected to a treatment with air before carrying out the process for the manufacture of 2,3,3,3-tetrafluoropropene.

The activation stages can be carried out at atmospheric pressure or under a pressure of up to 20 bar.

The activation of the catalysts can be carried out in the same reactor as the manufacturing process according to the present invention and exhibits the advantage of being more practical to carry out than in a fixed bed process.

The process of the present invention can comprise at least one noncontinuous regeneration stage in the presence of molecular oxygen. The temperature can vary between 250 and 500° C., the contact time can be between 1 and 200 s and the duration can preferably be between 10 and 200 h. The pressure at which the catalytic regeneration can be carried out is preferably between 1 and 20 bar abs.

The fluidized bed reactor is preferably equipped with heat exchangers immersed in the solid bed, so as to remove or supply the heat necessary for the reaction and/or regeneration, and also for the transient phases.

The invention claimed is:

1. A process for the manufacture of 2,3,3,3-tetra-fluoro-1-propene comprising at least one stage of gas-phase fluorination with HF of reactants comprising at least one compound selected from the group consisting of halopropanes of the formula $CX_3CHClCH_2X$ and halopropanes of the formulae $CX_3CCl=CH_2$, $CClX_2CCl=CH_2$ and $CX_2=CClCH_2X$, with X independently representing a fluorine or chlorine atom, in the presence of molecular oxygen and a fluorination catalyst held in suspension in a fluidized bed reactor.

2. The process of claim 1, wherein the molecular oxygen is in the form of air, enriched air or high-purity oxygen.

3. The process of claim 1, wherein the halopropane comprises 2,3-dichloro-1,1,1-trifluoropropane and/or 1,1,1,2,3-pentachloropropane.

4. The process of claim 1, wherein the halopropene of formula $CX_3CCl=CH_2$ comprises 2-chloro-3,3,3-trifluoro-1-propene.

5. The process of claim 1, wherein the oxygen compounds to be fluorinated molar ratio is between 0.01 and 1.

6. The process of claim 1, wherein the contact time between a gas mixture comprising the reactants and the catalyst is between 1 and 50 s.

7. The process of claim 1, wherein the catalyst comprises chromium.

8. The process of claim 7, wherein a mean diameter of the catalyst particles is between 20 and 200 microns.

9. The process of claim 1, wherein the catalyst is subjected to an activation stage.

10. The process of claim 1, wherein a flow of the reactants is injected tangentially into the reactor.

* * * * *